(12) United States Patent
Hupps

(10) Patent No.: US 10,413,713 B1
(45) Date of Patent: Sep. 17, 2019

(54) HOUSING DEVICE FOR RETRACTABLY HOUSING A MEDICAL TUBING

(71) Applicant: Brian Reese Hupps, Port St Lucie, FL (US)

(72) Inventor: Brian Reese Hupps, Port St Lucie, FL (US)

( * ) Notice: Subject to any disclaimer, the term of this patent is extended or adjusted under 35 U.S.C. 154(b) by 0 days.

(21) Appl. No.: 15/445,974

(22) Filed: Feb. 28, 2017

Related U.S. Application Data

(60) Provisional application No. 62/301,827, filed on Mar. 1, 2016.

(51) Int. Cl.
| | | |
|---|---|---|
| *B65H 75/44* | (2006.01) | |
| *A61M 39/08* | (2006.01) | |
| *A61M 39/10* | (2006.01) | |
| *B65H 75/48* | (2006.01) | |

(52) U.S. Cl.
CPC ............ *A61M 39/08* (2013.01); *A61M 39/10* (2013.01); *B65H 75/446* (2013.01); *B65H 75/4471* (2013.01); *B65H 75/4478* (2013.01); *B65H 75/486* (2013.01); *Y10T 137/6943* (2015.04)

(58) Field of Classification Search
CPC .......... Y10T 137/6943; B65H 75/4471; B65H 75/4478; B65H 75/486
See application file for complete search history.

(56) References Cited

U.S. PATENT DOCUMENTS

| | | | |
|---|---|---|---|
| 2,629,630 A * | 2/1953 | Roark | B65H 75/38 |
| | | | 137/355.17 |
| 3,940,843 A * | 3/1976 | Yeager | B23P 11/00 |
| | | | 285/354 |
| 4,685,456 A | 8/1987 | Smart | |
| 5,392,808 A | 2/1995 | Pierce | |
| 5,787,923 A * | 8/1998 | Shea | B65H 75/4402 |
| | | | 137/355.23 |
| 5,826,608 A | 10/1998 | Pierce | |
| 6,065,490 A | 5/2000 | Falcone | |
| 6,467,499 B1 * | 10/2002 | Smith | B65H 75/362 |
| | | | 137/355.16 |
| 7,104,491 B2 | 9/2006 | Vinding | |
| 8,746,246 B2 | 6/2014 | Lueckenhoff | |
| 2006/0243282 A1 | 11/2006 | Sackman et al. | |
| 2011/0017856 A1 | 1/2011 | Penn | |
| 2014/0166799 A1 | 6/2014 | Davis, Jr. et al. | |
| 2015/0069164 A1 | 3/2015 | Moore | |

* cited by examiner

*Primary Examiner* — Kevin F Murphy
(74) *Attorney, Agent, or Firm* — H. John Rizvi; The Patent Professor

(57) ABSTRACT

A medical tubing housing device is provided including a housing having a front housing portion, a rear housing portion and a spool of medical tubing rotatably mounted within the housing. A retraction mechanism, including a drive plate and a spiral torsion spring, is mounted within the housing between the spool and the rear housing portion and the drive plate is in engagement with the spool. An inlet is provided on the rear housing portion for receipt of an external fluid source and is in fluid communication with the supply tubing through a collar of the housing and a connecting portion rotatably attached to the collar. The spiral torsion spring is movable between an unstressed condition and a stressed condition when the spool is rotated as the medical tubing is pulled out of the housing. The medical tubing housing device may also include a wall mount to mount the housing to a stable surface.

18 Claims, 14 Drawing Sheets

HOUSING DEVICE FOR RETRACTABLY HOUSING A MEDICAL TUBING

CROSS-REFERENCE TO RELATED APPLICATIONS

This application claims the benefit of U.S. Provisional Patent Application Ser. No. 62/301,827, filed on Mar. 1, 2016, which is incorporated by reference herein in its entirety.

FIELD OF THE INVENTION

The present invention relates generally to oxygen or other fluid supply devices for medical use, and more particularly, to a device to automatically retract a length of medical tubing. The present invention is not only limited to oxygen tubing, but may be applied to any medical tubing, lines or cords that can be automatically retracted.

BACKGROUND OF THE INVENTION

It is important in many medical and surgical situations to maintain a supply of oxygen to a patient to assist the patient in breathing and to maintain a consistent oxygen level in the blood stream. Several devices have been developed over the years to provide the patient with a constant supply of oxygen. These devices may take the form of portable devices for those requiring a source of oxygen as they go about their daily lives. Alternatively, the devices may take the form of permanent or semi-permanent devices for use in doctor's offices or hospitals.

In the case of the permanent oxygen supply devices, the source of oxygen itself is typically a large canister or a central oxygen supply network extending throughout the offices or hospital rooms. These canisters or supply networks are essentially fixed within the rooms and include a port to connect a length of supply tubing to bring the oxygen from the source to the patient.

While such a fixed setup may initially seem convenient, the relatively long lengths of supply tubing necessary to reach the patient are often unwieldy causing them to get tangled around furniture, medical device support frames or a patient's bed located in the room. This poses several problems including, inter alia, kinking or bending of the supply tubing thereby dangerously cutting off the flow of oxygen to the patient, danger of strangulation of the patient, danger of falling due to tripping over the excess supply tubing, etc.

Accordingly, there is an established need for a device for managing and retaining a length of medical tubing used to supply oxygen or another fluid to a patient, to prevent at least one of the above described problems from occurring.

SUMMARY OF THE INVENTION

The present invention is directed to a medical tubing housing device for automatically retracting a length of fluid supply tube or medical tubing when not in use. The device generally includes a housing having an internal, rotatable spool operated by a spiral torsion spring. A medical tubing can be wound on the spool. A first end of the medical tubing can extend out of the housing. An opposite, second end of the medical tubing can in turn be rotatably connected to a collar of the housing and in fluid communication with a fluid inlet. The spiral torsion spring is loaded when the medical tubing is pulled out of the housing and the spool is rotated in a corresponding unwinding direction. The spiral torsion spring, when loaded, can case the spool to rotate in an opposite, winding direction to retract the medical tubing into the housing and wind the medical tubing back onto the spool. The medical tubing housing device may also include a wall mount to mount the housing to a stable surface.

In a first implementation of the invention, a medical tubing housing device comprises a housing delimiting an internal space. The housing includes a mounting cylinder projecting into the internal space, the mounting cylinder comprising an internal cavity. A spool is housed within the internal space of the housing and is rotatably mounted on the mounting cylinder. The spool carries a medical tubing having a first end extending out of the housing and a second end. A receiving collar is carried by the housing and extends into the internal cavity of the mounting cylinder. The receiving collar is in fluid communication with a fluid inlet of the housing. The device further includes a connecting portion rotatably attaching the second end of the medical tubing to the receiving collar. A retraction mechanism is positioned within the internal space of the housing, the retraction mechanism including a spiral torsion spring. A first end of the spiral torsion spring is connected to the housing and a second end of the spiral torsion spring is configured to apply a torque on the spool in a winding direction in which the medical tubing is wound into the housing and onto the spool. Pulling the medical tubing out of the housing rotates the spool in an unwinding direction opposite to the winding direction and moves the spiral torsion spring from a first unstressed condition to a second stressed condition in which the spiral torsion spring biases the spool to rotate in the winding direction.

In a second aspect, the retraction mechanism can further include a drive plate. The second end of the spiral torsion spring can be configured to apply a torque on the drive plate. The drive plate can be configured to transfer the torque to the spool and can be rotatable in unison with the spool.

In another aspect, the spiral torsion spring can be arranged within a space delimited by a rear face of the drive plate and a circumferential flange extending rearwardly from the rear face of the drive plate.

In another aspect, the inlet can extend outwardly from the housing at a right angle relative to the housing.

In another aspect, the housing can include a front, first housing portion and a rear, second housing portion. The first housing portion can be movable relative to the second housing portion from a closed position in which the first housing portion prevents access to the internal space of the housing to an open position in which the first housing portion is moved away from the second housing portion and allows accessing the internal space of the housing.

In yet another aspect, the mounting cylinder can protrude from the second housing portion.

In another aspect, the first housing portion can be pivotably connected to the second housing portion.

In another aspect, the inlet can be arranged on a rear side of the second housing portion.

In another aspect, the spiral torsion spring can be connected at the first end thereof to the second housing portion.

In another aspect, the retraction mechanism can be positioned between the spool and the second housing portion.

In another aspect, the housing can include a latch mechanism comprising a first latch member on the first housing portion and a second latch member on the second housing portion. The first and second latch members can be engageable to secure the second housing portion in the closed position.

In yet another aspect, the medical tubing housing device can further include a wall mount attached to the second housing portion, the wall mount comprising a flat rear side for resting on a wall or other flat surface.

In another aspect, the wall mount can comprise a first wall mount portion and a second wall mount portion pivotably attached to the first wall mount portion. The first wall mount portion can be attached to the second housing portion, and the second wall mount portion can provide the flat rear side for resting against a wall or other flat surface.

In another aspect, the medical tubing housing device can further include at least one circumferential sealing gasket positioned between the receiving collar and the connecting portion.

In another aspect, the spool can be removably mounted on the mounting cylinder and removable from the housing.

In another aspect, the spool can include an inner plate and an outer plate extending in a spaced-apart relationship from a central drum of the spool, wherein the medical tubing is wound around the central drum and between the inner and outer plates.

In yet another aspect, the inner plate and the outer plate of the spool can be separated from one another a distance which is less than three times a diameter of the medical tubing. Preferably, this distance is greater than twice the diameter of the medical tubing.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a medical tubing housing device that is capable of tensioning and automatically retracting a length of medical fluid supply tube into a housing in a simple and economical manner in order to manage any excess length of the supply tubing when the full, overall length of the supply tubing is not needed to reach a patient.

Figure 1:
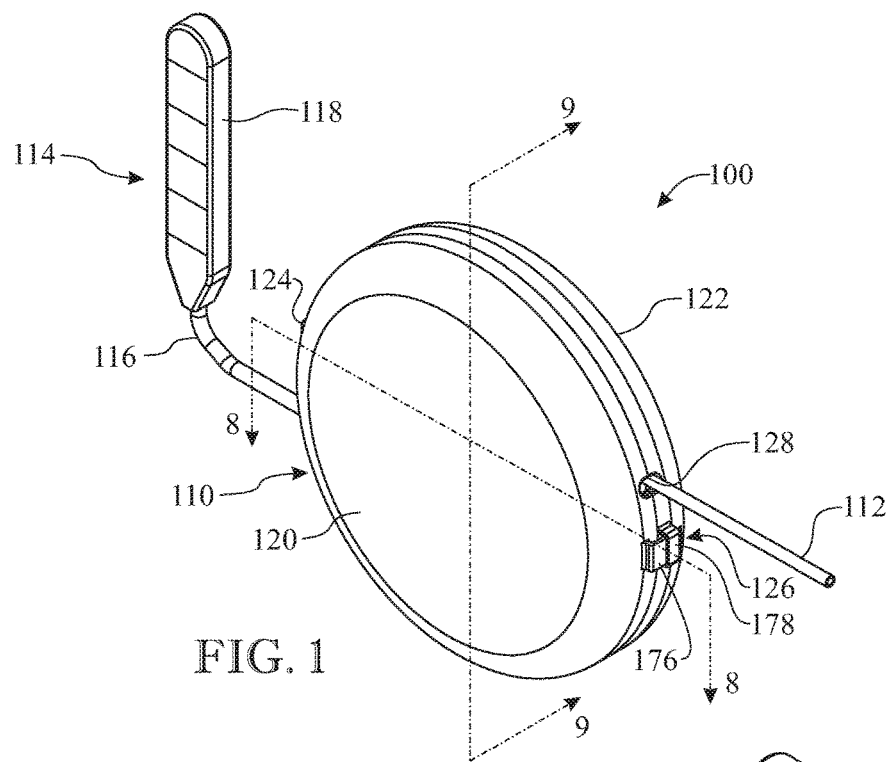
FIG. 1 presents an isometric front view of an illustrative embodiment of a medical tubing housing device in accordance with the present invention, and an associated fluid (e.g., oxygen) supply system.
Figure 2:
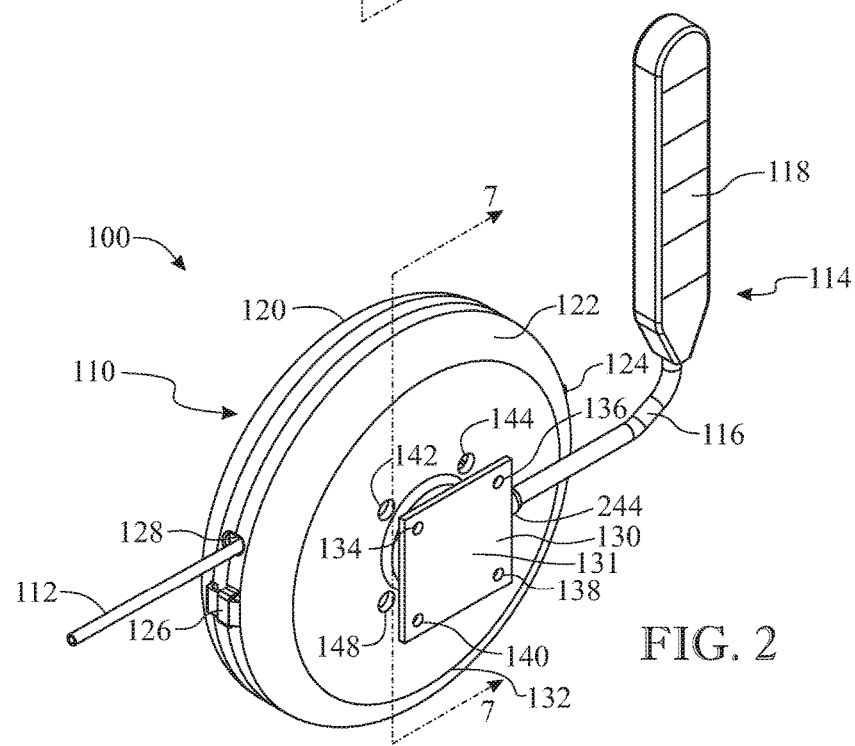
FIG. 2 presents an isometric rear view of the medical tubing housing device and the associated fluid supply system.

Referring to FIGS. 1-8, and initially to FIGS. 1 and 2, a medical tubing housing device 100 is illustrated in accordance with an exemplary embodiment of the present invention. The medical tubing housing device 100 generally includes a housing 110 comprising an internal space 111, and a relatively long length of a medical tubing or fluid supply tube 112 retractably storable in the internal space 111 of the housing 110. The fluid supply tube 112 receives a fluid (e.g., oxygen) from an external fluid source 114 and transfers the fluid to various devices for supplying the fluid to a patient (not shown). These devices may include, for example, oxygen masks, intravenous delivery devices, etc.

The external fluid source 114 includes a fluid feed tube 116 which is removably connected to the medical tubing housing device 100. The fluid feed tube 116 transfers fluid from an external source, such as for example, an oxygen tank or central oxygen supply system, to the fluid supply tube 112. A pressure meter 118 may be provided to measure the pressure in the fluid feed tube 116 prior to the fluid reaching the medical tubing housing device 100.

The housing 110 of the medical tubing housing device 100 is provided to retain the fluid supply tube 112 and generally includes a pair of housing portions or halves such as, for example, front housing portion or half 120 and rear housing portion or half 122 which are connected together in clamshell like fashion, delimiting the internal space 111 of the housing 110. In this embodiment, the front housing half 120 and the rear housing half 122 are pivotally connected by a hinge 124, as shown for instance in FIG. 3. As shown in FIG. 1, a latch 126 is provided on the front and rear housing halves 120 and 122, respectively, to maintain the housing halves in a closed condition adjacent each other to retain and protect the fluid supply tube 112. Alternative embodiments are contemplated for attaching or interlocking the front and rear housing halves 120 and 122; for instance and without limitation, the front and rear housing halves 120 and 122 can be connected to one another by a threaded connection, a twist-lock connection, a frictional fitting, or a snapped connection.

Referring to FIG. 2, the medical tubing housing device 100 can be used as a standalone device which is hand held by a user or can be mounted to an external surface for stability. In this embodiment, the medical tubing housing device 100 includes a mounting plate or wall mount 130 attached to the housing 110 for attaching the housing 110 to a sturdy flat surface (not shown) such as, for example, a table or wall of a patient's room. Specifically, the wall mount 130 is attached to, and extends from, a rear outer surface 132 of the rear housing half 122 and comprises a flat rear side 131 for resting on a wall or other flat surface. The wall mount 130 includes mounting holes 134, 136, 138 and 140 allowing the wall mount 130 to be bolted, screwed or otherwise fastened to an external surface. Access holes 142, 144, 146 and 148, corresponding to and aligned with the mounting holes 134, 136, 138 and 140 in the wall mount 130, respectively, are provided through the rear housing half 122 to allow the user to pass a mounting tool (e.g., a screwdriver) through the rear housing half 122 and secure the wall mount 130 to the external surface.

Figure 3:
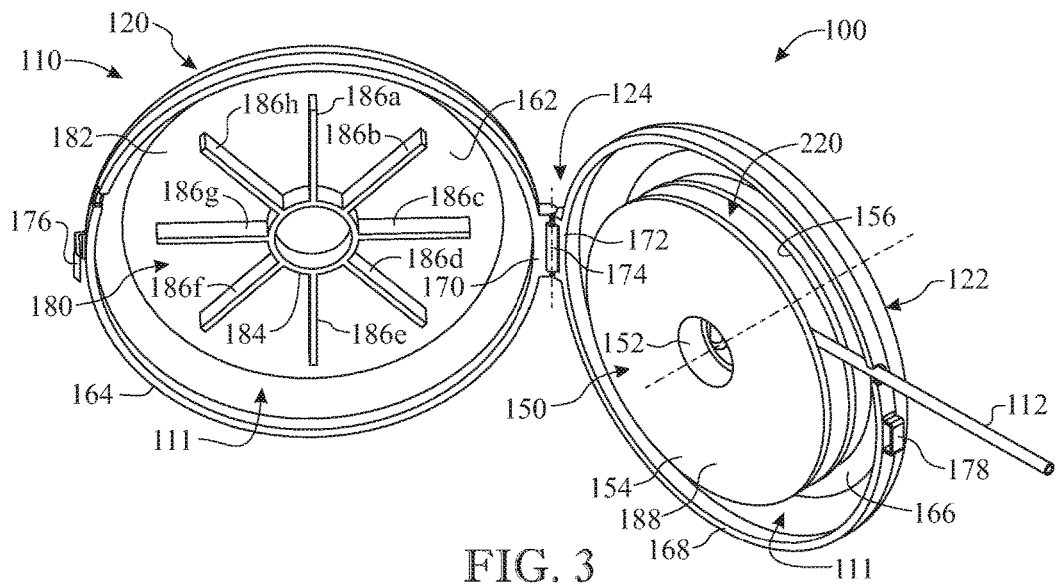
FIG. 3 presents an isometric view of the medical tubing housing device, with a housing of the device in an open position.
Figure 4:
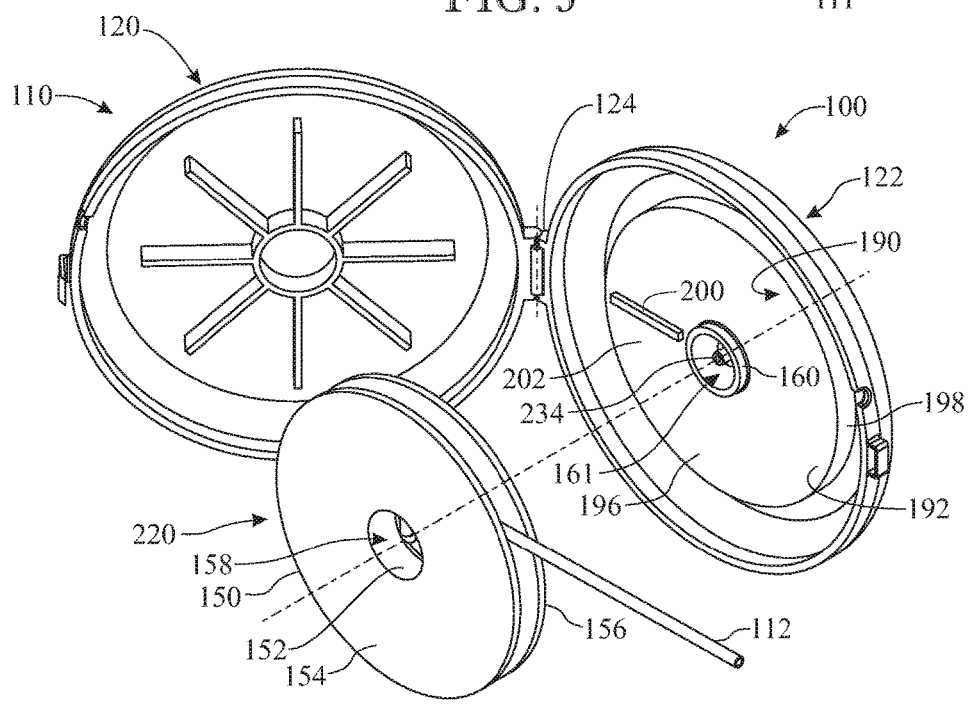
FIG. 4 presents an isometric view of the medical tubing housing device with a drum and fluid supply tube of the device removed from the housing.

Referring now to FIGS. 3 and 4, the medical tubing housing device 100 includes a reel or spool 150 for retaining a length of the fluid supply tube 112. The spool 150 is arranged in the internal space 111 of the housing 110, and includes a central hub or drum 152 and spaced apart circular outer and inner side plates 154 and 156 extending from the drum 152. The fluid supply tube 112 is wound around the drum 152 and maintained on the drum by the outer and inner side plates 154 and 156. As discussed in more detail hereinbelow, the outer and inner side plates 154 and 156 are preferably spaced apart a pre-determined distance equal to or just slightly greater than twice the diameter of the fluid supply tube 112 and substantially less than three times the diameter of the fluid supply tube 112 so that only two side-by-side windings of the fluid supply tube 112 fit between the outer and inner side plates 154 and 156. By allowing only two side-by-side windings of the fluid supply tube 112 on the drum 152, the chances of binding of the fluid supply tube 112 on itself are minimized. As best shown in FIG. 4, the spool 150 further includes a central bore 158, extending centrally through the drum 152, the outer side plate 154 and the inner side plate 156, for receipt of a mounting cylinder 160. The mounting cylinder 160 extends inwardly (i.e. into the internal space 111 of the housing 110) from the rear housing half 122 to rotatably support the spool 150 within the housing 110. The mounting cylinder 160 is formed by a cylindrical wall enclosing an internal cavity 161.

With specific reference to FIG. 3, the front housing half 120 includes a central disk 162 having a circumferential inwardly-directed flange 164 and the rear housing half 122 also includes a central disk 166 and a circumferential inwardly-directed flange 168. The first and second housing halves 120 and 122 are pivotally connected together to access the spool 150 and include a first hinge portion 170 on the first housing half 120 and a second hinge portion 172 on the second housing half 122. The first and second hinge portions 170 and 172 are connected together by a central pivot pin 174 (also shown in FIG. 8). Thus, the first and second housing halves 120 and 122 are movable from a first position in which they are clamped together about the spool 150 (FIG. 1) to a second position in which they are spaced apart (FIG. 3) for access to the spool 150 for removal and/or replacement. As shown in FIG. 3, the latch 126 includes a first or male latch member 176 extending from the circumferential flange 164 of the first housing half 120 and a second or female latch member 178 extending from the circumferential flange 168 of the rear housing half 122. The male latch member 176 is slightly flexible and engages the female latch member 178 in snap fit fashion to maintain the front and rear housing halves 120 and 122 together during use.

The front housing half 120 additionally includes a spool support 180, extending from an inner surface 182 of the disk 162 of the front housing half 120, for maintaining the spool 150 on the mounting cylinder 160. In some embodiments, such as the embodiment depicted herein, the spool support 180 can include a central hub 184 having a plurality of support fingers or ribs 186*a-h* which press against an outer face 188 of the outer side plate 154 of the spool 150.

Figure 5:
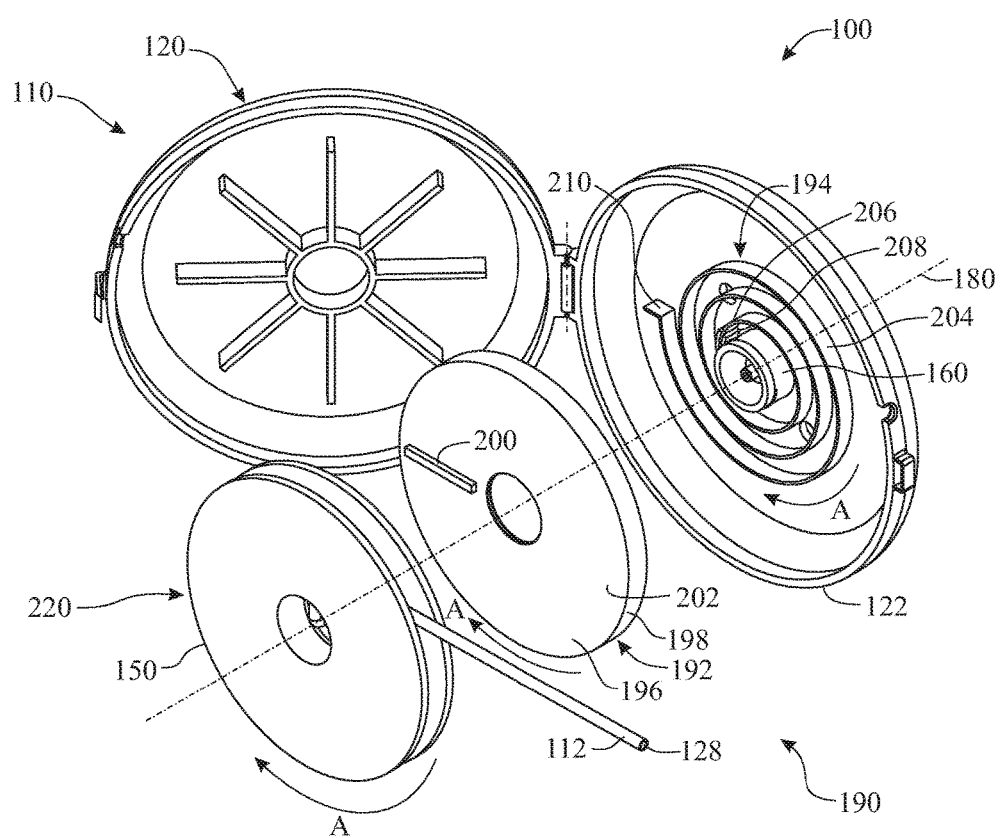
FIG. 5 presents an isometric view of the medical tubing housing device with the drum and fluid supply tube and a disk of a spring mechanism of the device removed from the housing.
Figure 6:
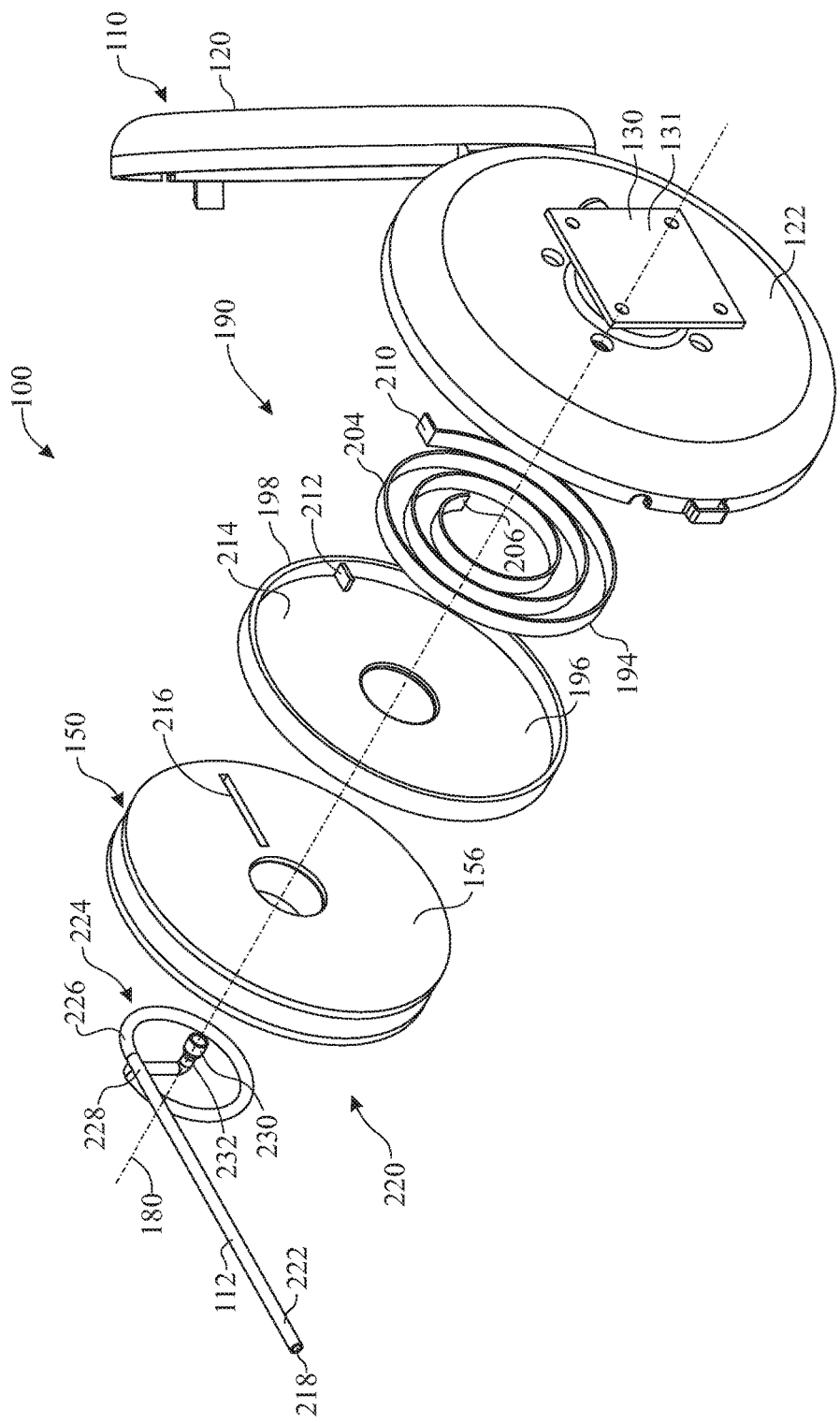
FIG. 6 presents an isometric rear exploded view of the medical tubing housing device.

Turning now to FIGS. 4-6, in order to tension the spool 150 and automatically retract the fluid supply tube 112 within the housing 110, the medical tubing housing device 100 additionally includes a spring-biased retraction mechanism 190 also mounted over the mounting cylinder 160. The retraction mechanism 190 generally includes a drive plate 192 and a spiral torsion spring 194 positioned between the drive plate 192 and the rear housing half 122 (FIG. 5). As best understood from FIG. 6, the drive plate 192 houses the spiral torsion spring 194 and includes a base or disk 196 and an outwardly and rearwardly directed circumferential sidewall or flange 198. As shown in FIG. 5, a radially extending drive bar 200 is positioned on and protrudes from a front, first face 202 of the disk 196. The drive bar 200 engages the spool 150 and rotates the spool 150 within the housing 110 in response to the spiral torsion spring 194.

As shown in FIGS. 5 and 6, the spiral torsion spring 194 is formed as a coil from a length or strip 204 of flat, elastic, resilient or shape memory alloy or material. The strip 204 is shaped as a coil that has a first or unstressed condition (FIGS. 5 and 6) and a second, tighter coiled or stressed condition. Being formed from an elastic, resilient or shape memory material the strip 204 naturally wants to return from the second stressed condition to the first unstressed condition. The strip 204 includes an inner, first end 206 which is anchored to the mounting cylinder 160 by a clip 208 (FIG. 5) and an outer, bent second end 210 which engages a radially-inwardly directed tab 212 protruding rearwardly from the disk 196 (FIG. 6). The radially-inwardly directed tab 212 extends radially inwardly from the circumferential flange 198 and along a rear, second face 214 of the disk 196.

As noted above, the retraction mechanism 190 is provided to tension the spool 150 and automatically retract the fluid supply tube 112 into the housing 110. Rotation of the spiral torsion spring 194 clockwise in the direction of arrow "A", as viewed in FIG. 5, compresses and coils or tensions the spiral torsion spring 194 about the mounting cylinder 160. With regard to FIG. 6, the inner side plate 156 of the spool 150 includes a radial slot 216 which removably receives the drive bar 200 (FIG. 5) which protrudes frontward from the disk 196 of the drive plate 192. Thus, as the spool 150 is also rotated in the direction of arrow "A", which corresponds to pulling a first end of the fluid supply tube 112 out of the housing and unwinding the fluid supply tube 112 off the spool 150, the spool 150 rotates and tensions the retraction mechanism 190. This puts the spiral torsion spring 194 in the second stressed condition. Release of the fluid supply tube 112 allows the spiral torsion spring to return to the first or unstressed condition rotating the drive plate 192 in a direction opposite to arrow "A" and thus the spool 150 to pull the fluid supply tube 112 back into the housing 110.

It should be noted that, in different embodiments of the invention, the retractable medical tubing device 100 may be provided with or without the fluid supply tube 112. In addition, as mentioned heretofore, the spool 150 containing the fluid supply tube 112 is removable from the housing 110 for replacement; thus, the spool 150 and the fluid supply tube 112, together, can form a replaceable tubing cartridge 220. This allows a fresh, clean length of fluid supply tube 112 to be provided for subsequent uses of the medical tubing housing device 100. It should also be noted that the remaining components of the medical tubing housing device 100, including but not limited to the housing 110 and the retraction mechanism 190, can be formed from an easily sterilizable material such as, for example, stainless steel, etc.

The fluid supply tube 112 is formed from a flexible, biocompatible material such as, for example, a polymeric material. With specific reference to FIG. 6, the fluid supply tube 112 can include a first, flexible length of supply tubing 222 and a second, pre-formed coiled section 224. The coiled section 224 has a first end 226 connected to a second end 228 of the supply tubing 222. A connector 230 is provided on an inwardly bent second end 232 of the coiled section 224 and is engagable with a rotatable connecting portion (consisting in a rotatable nipple 234 (FIG. 4)) extending inwardly from the second housing half 122. The inwardly bent second end 232 is formed at a right angle to the remainder of the coiled section 224. It should be noted that the inwardly bent second end 232, the spool 150, the retraction mechanism 190, the mounting cylinder 160 and the rotatable nipple 234 are all co-axial about a common central axis 180.

Figure 7:
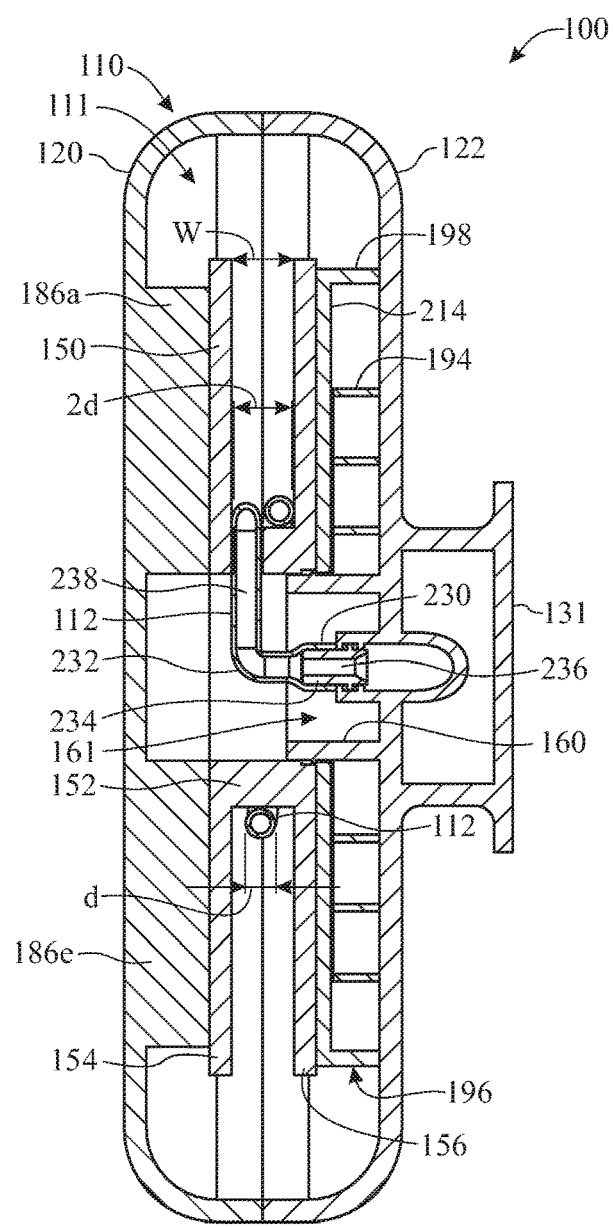
FIG. 7 presents a cross-sectional side elevation view of the medical tubing housing device, taken along section plane 7-7 indicated in FIG. 2.
Figure 8:
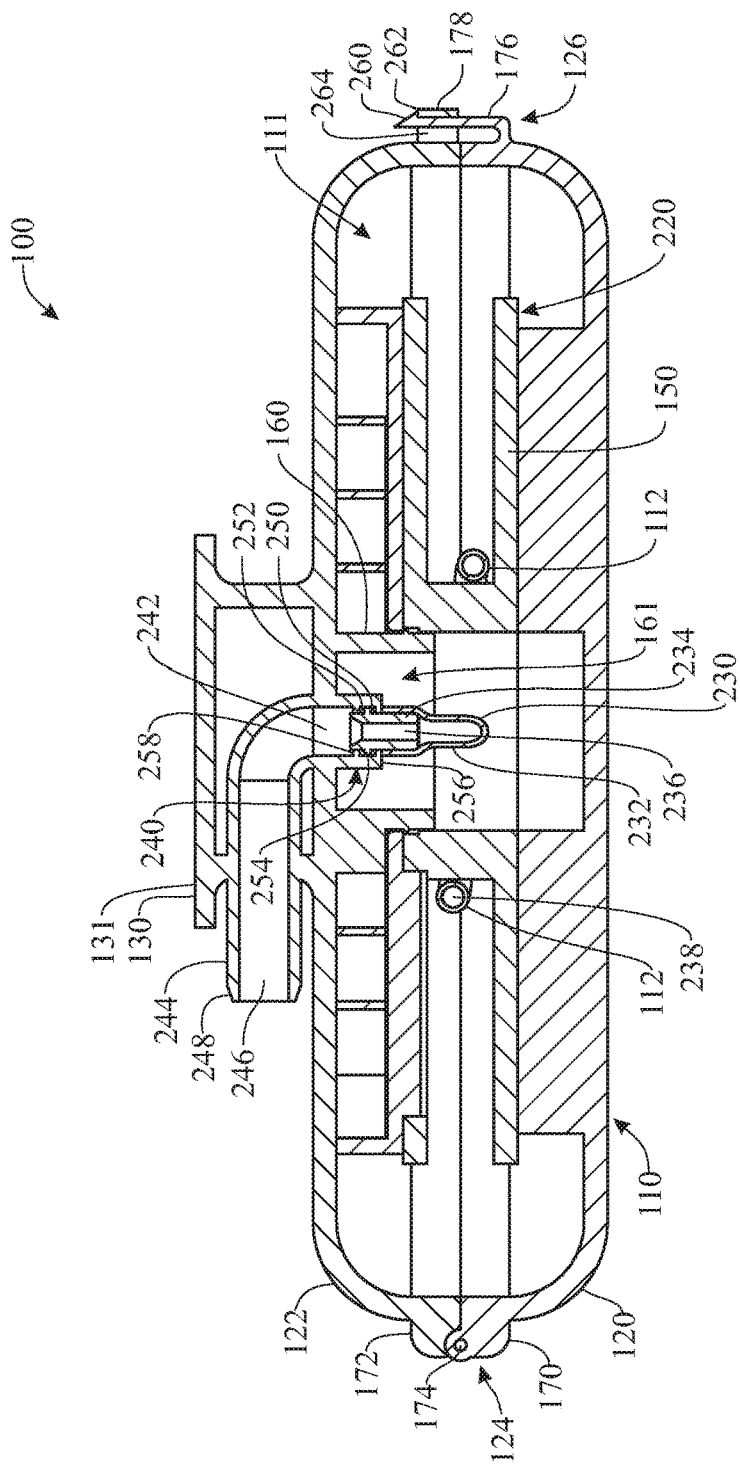
FIG. 8 presents a cross-sectional top plan view of the medical tubing housing device, taken along section plane 8-8 indicated in FIG. 1.

Turning now to FIGS. 7 and 8, it can be observed that the rotatable nipple 234 is arranged in the internal cavity 161 of the mounting cylinder 160. The rotatable nipple 234 is hollow, having a bore 236 which is in fluid communication with a hollow interior 238 of the fluid supply tube 112 when the fluid supply tube 112 is connected to the rotatable nipple 234. The rotatable nipple 234 allows the fluid supply tube 112 to be unwound off or onto the spool 150 while maintaining a sealed connection with the fluid feed tube 116 of the external fluid source 114 as described below.

As best shown in FIG. 7, and as noted above, a width "W" between the outer side plate 154 and the inner side plate 156 is slightly greater than two times the outer diameter "d" of the fluid supply tube 112 but less than three times the outer diameter "d" of the fluid supply tube 112. Thus, only two side-by-side windings of the fluid supply tube 112 fit between the outer and inner side plates 154 and 156, respectively, in any horizontal layer of windings of the fluid supply tube 112 to prevent binding or cinching of the fluid supply tube 112 against itself within the spool 150.

With specific reference to FIG. 8, the rotatable, hollow nipple 234 is rotatably mounted to and within a receiving collar 240, which is arranged extending from the rear housing half 122 into the internal cavity 161 of the mounting cylinder 160. Specifically, the hollow nipple 234 extends through a bore 242 of the receiving collar 240 and is in fluid communication with an inlet 244 formed as a rigid 90-degree tube extending outwardly from the rear housing half 122, generally between the rear housing half 122 and the wall mount 130. The hollow bore 236 of the nipple 234 is in fluid communication with a through bore 246 of the inlet 244. A free, open end 248 of the inlet 244 is configured to receive the fluid feed tube 116 (FIG. 2) in friction fit fashion, for instance and without limitation.

In order to rotatably support the nipple 234 within the receiving collar 240 while maintaining a sealed condition against fluid leakage, a pair of rings or sealing gaskets 250 and 252 are seated within the receiving collar 240 and adjacent either side of a circumferential flange 254 on an outer surface 256 of the rotatable nipple 234. The flange 254 of the nipple 234 and the gaskets 250 and 252 are secured within the receiving collar 240 between inner and outer inwardly directed circumferential plates 256 and 258 of the receiving collar 240. The circumferential flange 254 of the nipple 234 is rotatably mounted within the receiving collar 240. This allows the nipple 234 to rotate within the receiving collar 240 while maintaining a fluid tight seal with the receiving collar 240 and the inlet 244.

As more clearly shown in FIG. 8, the flexible male latch member 176 extends through the female latch member 178 when the front and rear housing halves 120 and 122, respectively, are moved to a closed condition adjacent each other. A hook or barb 260 engages an edge 262 of the female latch member 178 when the male latch member 176 passes through an inner slot 264 of the female latch member 178 to maintain the housing 110 in a closed condition. Pressing the barb 260 inwardly releases the male latch member 176 from the female latch member 178 thereby allowing the front and rear housing halves 120 and 122, respectively, to be moved or pivoted about the hinge 124 to an open condition to remove and/or replace the replaceable tubing cartridge 220.

Referring now to FIGS. 1-6 and 9-10, to use the medical tubing housing device 100, the front and rear housing halves 120 and 122 are moved to the open position by releasing the latch 126 and pivoting them to the open position (FIGS. 3 and 4). If the medical tubing housing device 100 is to be mounted to a wall or other stable surface, the retraction mechanism is removed and fasteners (not shown) are used to secure the wall mount 130 (FIG. 2) to the surface as described above and the retraction mechanism 190 mounted back over the mounting cylinder 160.

A fresh or clean replaceable tubing cartridge 220, containing the desired type and size of the fluid supply tube 112 is inserted into the housing 110 and mounted on the mounting cylinder 160 such that the drive bar 200 on the retraction mechanism 190 (FIG. 5) engages the radial slot 216 in the spool 150 (FIG. 6) of the replaceable tubing cartridge 220.

The front and rear housing halves 120 and 122 are then pivoted to the closed condition and secured by the engagement of the male latch member 176 with the female latch member 178 (FIG. 1). The medical tubing housing device 100 is then connected to the external fluid source 114 by inserting the fluid feed tube 116 to the inlet 244 (FIGS. 2 and 8).

Figure 9:
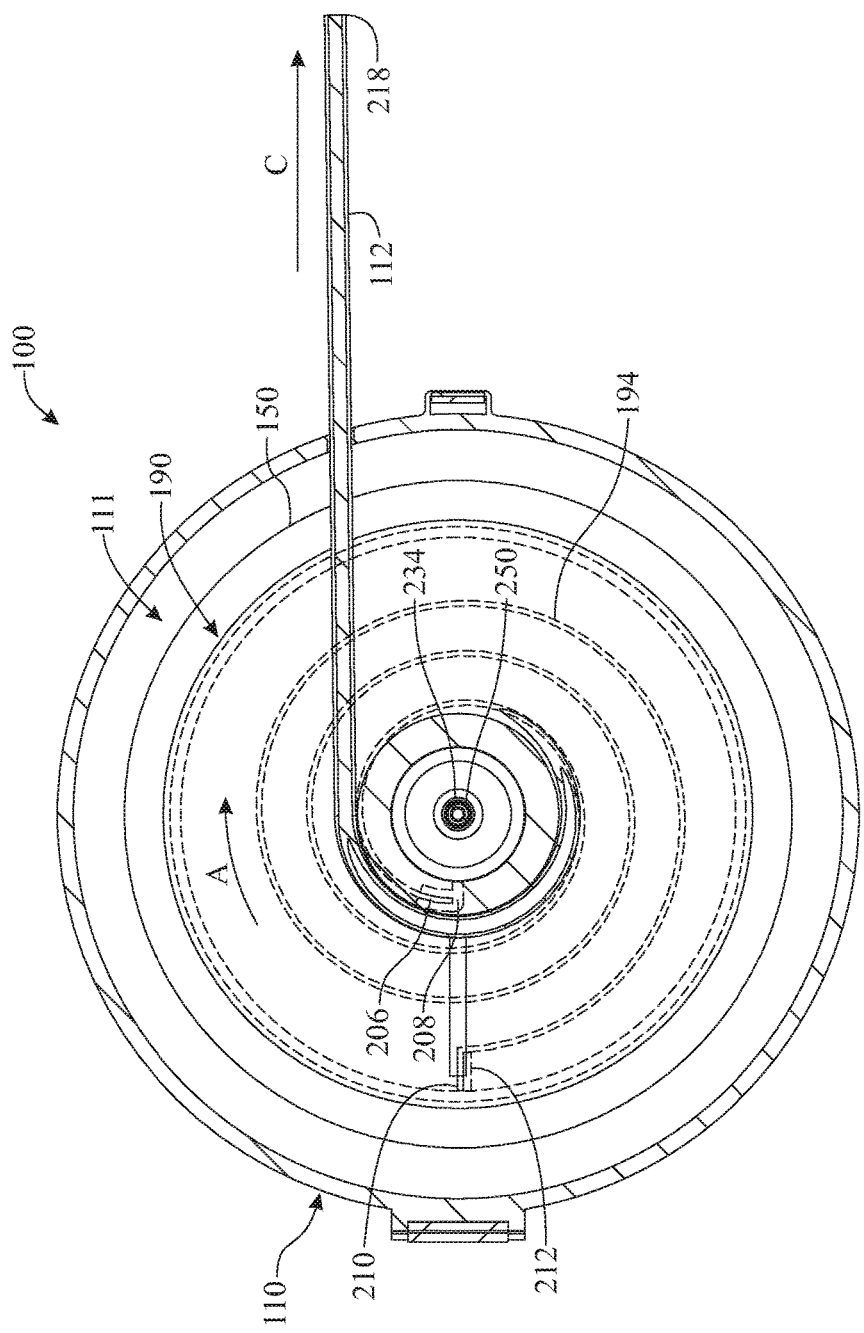
FIG. 9 presents a cross-sectional front elevation view of the medical tubing housing device, taken along section plane 9-9 indicated in FIG. 1.

With reference to FIG. 9, in order to use the medical tubing housing device 100 to reach and supply fluid to a remote device, the first end 218 of the fluid supply tube 112 is pulled out of the housing in the direction of arrow "C". Pulling the fluid supply tube 112 rotates the spool 150 in the direction of arrow "A" thereby rotating the retraction mechanism 190 and coiling the spiral torsion spring 194 into the second or stressed condition. The first end 218 of the fluid supply tube 212 is then connected to the external device and the external fluid source 114 turned on to supply fluid to the external device. As noted hereinabove, there is no leakage of fluid as the nipple 234 rotates within the receiving collar 240 due to the seal provided by the gaskets, for example gasket 250. Fluid flows through the fluid feed tube 116, through the inlet 244 (FIGS. 2 and 8) and into and through the hollow bore 236 of the nipple 234. The fluid passes though the nipple 234, through the fluid supply tube 112 and into the external device (not shown). The fluid pressure through the system may be monitored with the pressure meter 118.

Figure 10:
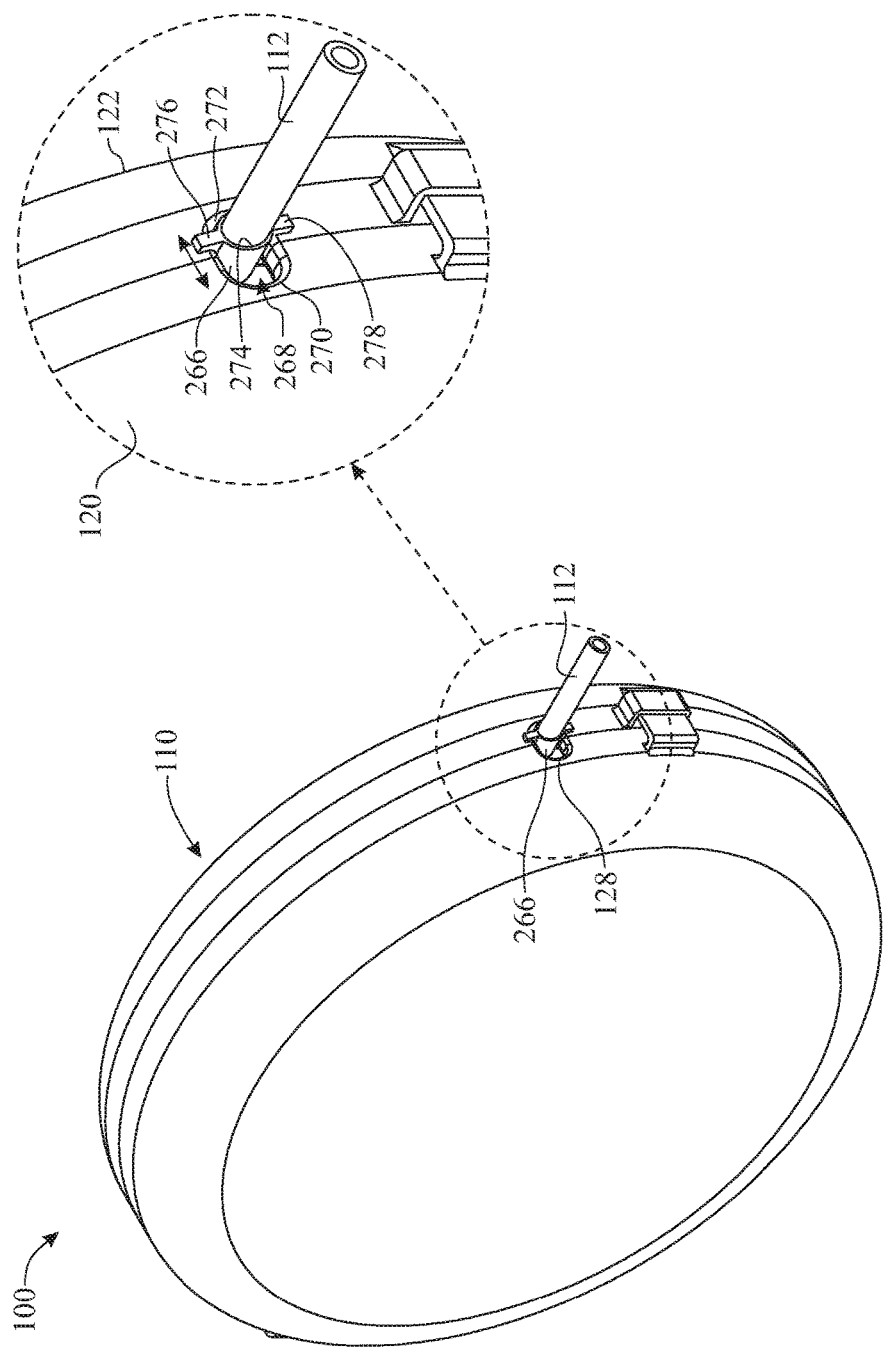
FIG. 10 presents an isometric view of the medical tubing housing device of FIG. 1, provided with an optional sliding support sleeve, the view including an enlarged area of detail of the optional sliding support sleeve.

With reference to FIG. 10, a sliding support sleeve 266 may be provided through the tube outlet opening 128 in the housing 110 to guide the fluid supply tube 112 as the two side-by-side layers of the fluid supply tube 112 are wound and unwound on the spool 150. The support sleeve 266 can oscillate back and forth across an oval slot 268 formed in the tube outlet opening 128 by the outlet opening halves 270 and 272 formed in the front and rear housing halves 120 and 122, respectively. Specifically, the support sleeve 266 has a through bore 274 through which the fluid supply tube 112 passes and a pair of tabs 276 and 278 extending radially outward from the support sleeve 266 to guide the support sleeve 226 within the tube outlet opening 128. While not specifically shown, a locking mechanism may be provided to engage the fluid supply tube 112 and maintain the fluid supply tube 112 in a pulled out or extended condition, against the tension of the retraction mechanism 190 until released.

Once the supply of fluid is no longer needed, the external fluid source 114 is turned off and the fluid supply tube 112 is disconnected from the external device. Any provided tube locking mechanism can be released and the fluid supply tube 112 is automatically retracted back into the housing 110 by the retraction mechanism 190. Specifically, once the outward pull or pressure is removed from the fluid supply tube 112, the spiral torsion spring 194 (FIG. 9) is free to return to its first or unstressed condition rotating the drive plate 192 and thereby rewinding the fluid supply tube 112 back around the spool 150. Thereafter, the housing 110 can be opened and the replaceable tubing cartridge 220 removed for sterilization or replacement.

In this manner, the medical tubing housing device 100 provides a novel and useful device for managing a length of fluid supply tube 112 to avoid kinking or danger to people in the immediate vicinity.

Alternative embodiments to the illustrated embodiment are contemplated, without departing from the scope of the invention. For instance, in some embodiments, the wall mount may be arranged on a different area or portion of the housing 110 such as on a front surface of the front housing half 120, or on a side of the housing 110. In other embodiments, alternatively to having a fixed wall mount (such as the fixed-plate wall mount 130 depicted herein), the retractable medical tubing device can include a movable wall mount allowing the housing to move, when attached to a wall or surface by means of the wall mount. For instance, the wall mount can be articulated or hinged.

Figure 11:
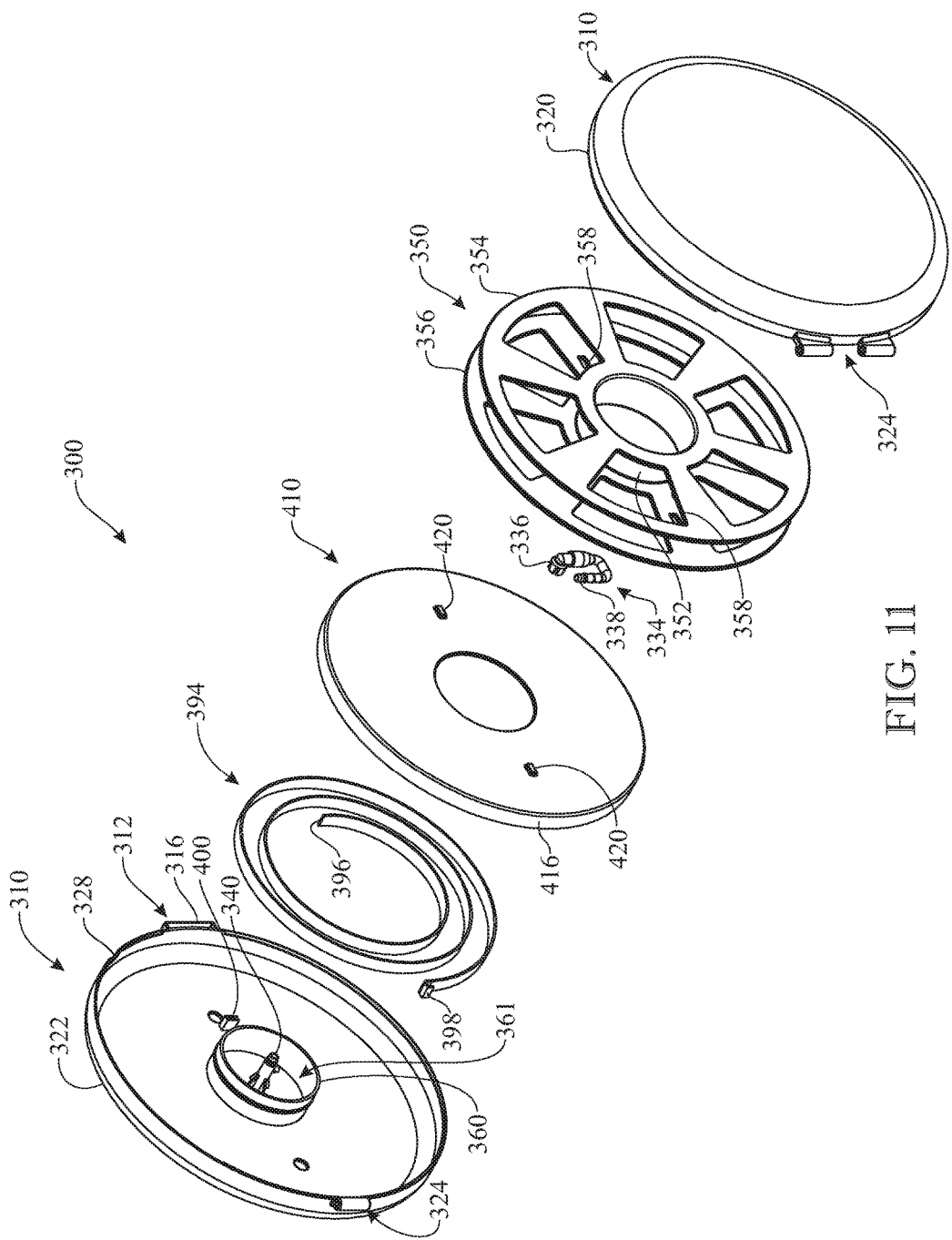
FIG. 11 presents a top front exploded view of a medical tubing housing device in accordance with a second illustrative embodiment of the invention.
Figure 12:
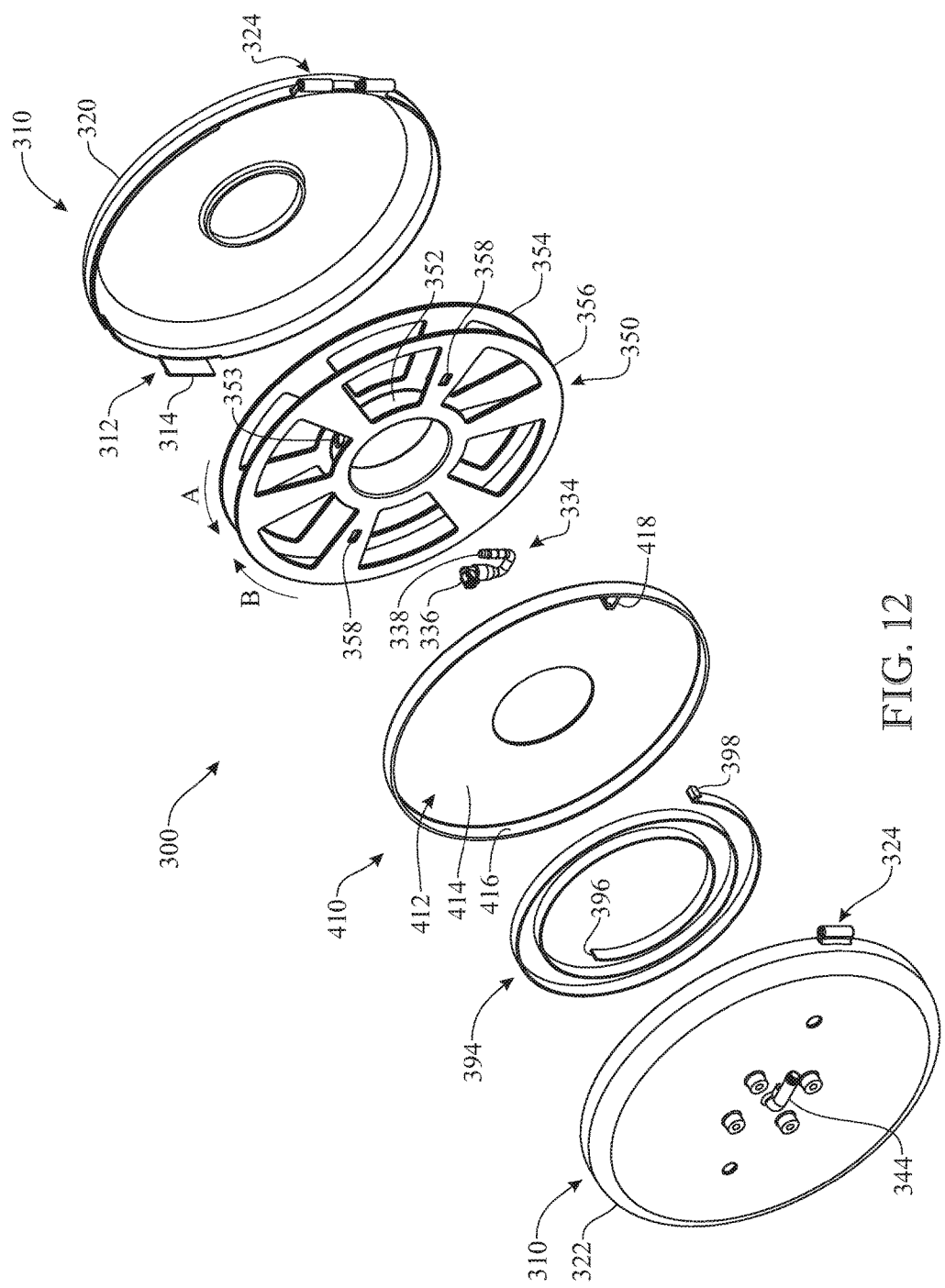
FIG. 12 presents a top rear exploded view of the medical tubing housing device of FIG. 11.
Figure 13:
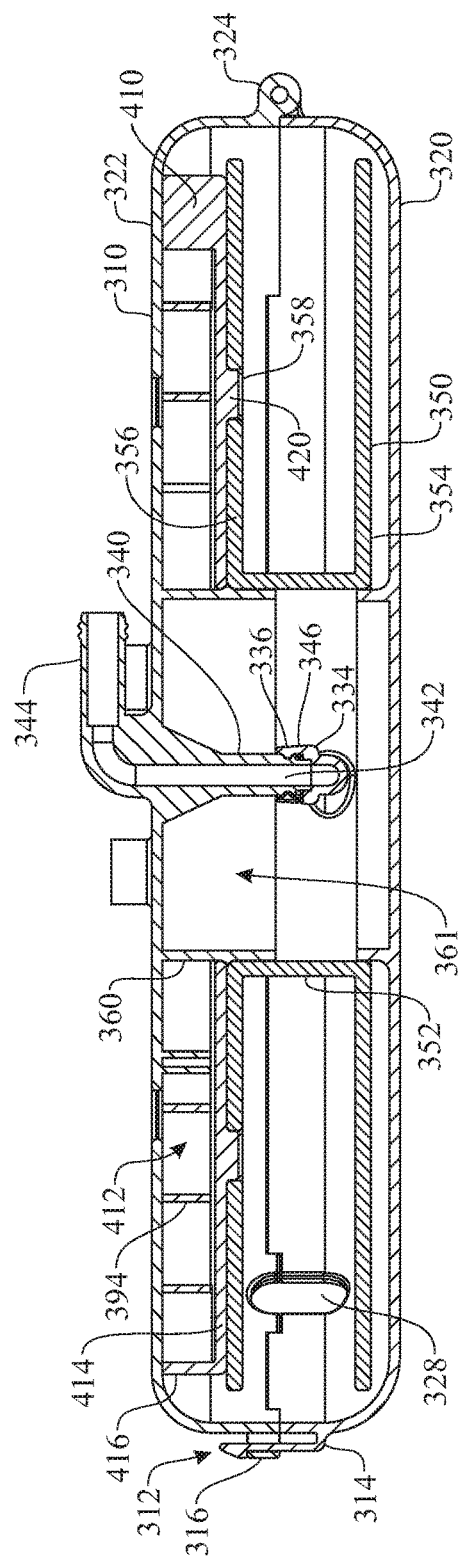
FIG. 13 presents a cross-sectional, bottom plan view of the medical tubing housing device of FIG. 11, the cross section taken along section plane 13-13 indicated in FIG. 14.
Figure 14:
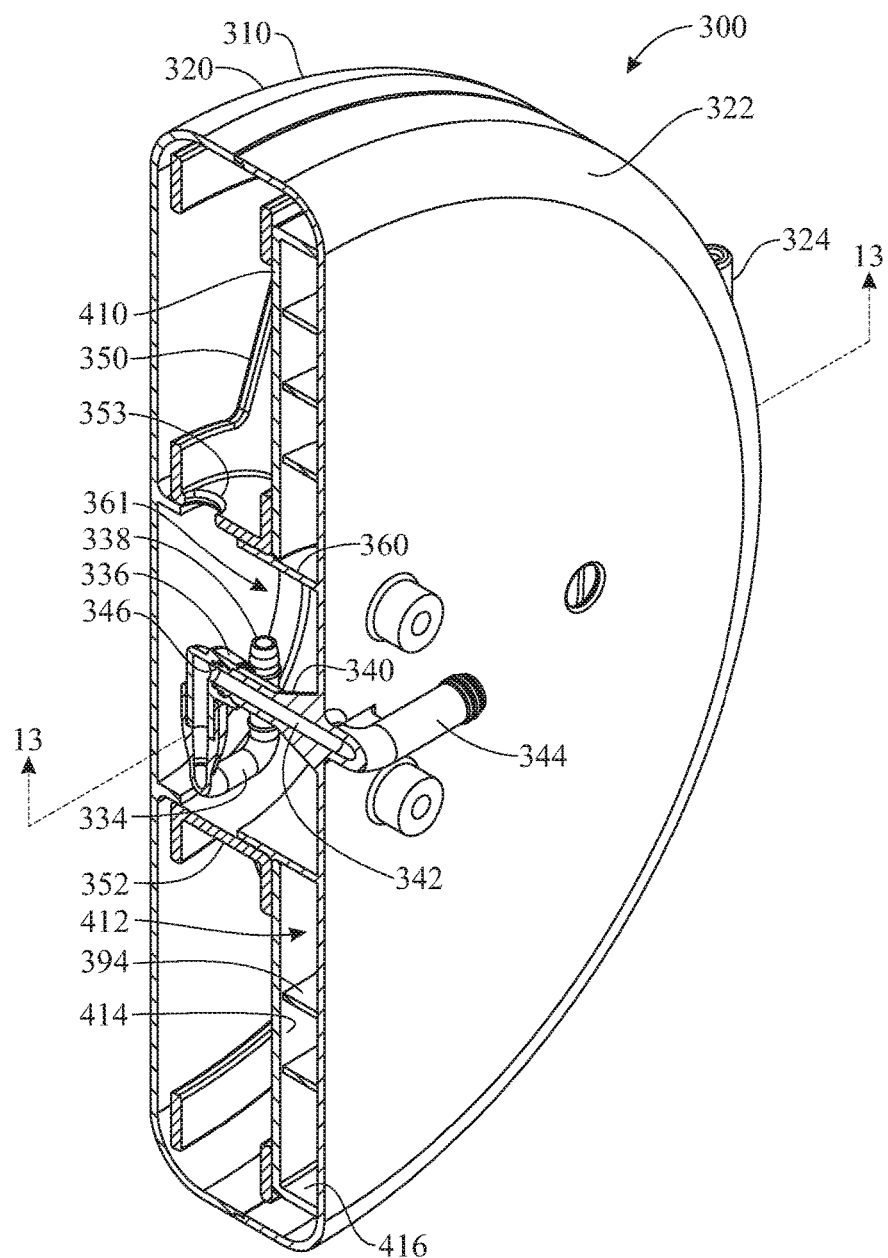
FIG. 14 presents a cross-sectional, top rear perspective view of the medical tubing housing device of FIG. 11.

The illustrations of FIGS. 11 through 14 present a medical tubing housing device 300 in accordance with another embodiment of the invention. Similarly to the previous embodiment, the medical tubing housing device 300 comprises a housing 310 delimiting an internal space 311. The housing 310 is formed of a first or front housing portion 320 and second or rear housing portion 322, formed in a clamshell fashion to delimit the internal space 311 of the housing 310. The front housing portion 320 is movable relative to the rear housing portion 322, and more specifically, is pivotally movable about a hinge 324. The front housing portion 320 can pivot from a closed position (FIGS. 13 and 14) in which the front housing portion 320 prevents access to the internal space 311 of the housing 310 to an open position (similar to the open position depicted in FIG. 3 with reference to the previous embodiment) in which the front housing portion 320 is moved away from the rear housing portion 322 and allows accessing the internal space 311 of the housing 310. The housing 310 further includes a latch mechanism or latch 312 including a first latch member 314 on the front housing portion 320 and a second latch member 316 on the rear housing portion 322, the first and second latch members 314 and 316 engageable to secure the rear housing portion 322 in the closed position as shown in FIG. 13.

As shown in FIG. 11, the housing 310 includes a mounting cylinder 360 projecting into the internal space 311. Specifically, the mounting cylinder 360 protrudes from the rear housing portion 322 and includes an internal cavity 361, best shown in FIGS. 11 and 13. As further shown in FIGS. 11 and 12, similarly to the previous embodiment, the medical tubing housing device 300 further includes a spool 350 for carrying a medical tubing; while not specifically shown, the medical tubing can be similar to the medical tubing (i.e. the fluid supply tube 112) of the previous embodiment and, similarly to said fluid supply tube 112, can have a first end extending out of the housing 310 (through a tube outlet opening 328 in the housing 310) and a second end located within the housing 310. The spool 350 is housed within the internal space 311 of the housing 310 and is rotatably mounted on the mounting cylinder 360, allowing to wind the medical tubing thereon and unwind the medical tubing therefrom. For this purpose, the spool 350 includes an outer plate 354 and an inner plate 356 extending in a spaced-apart relationship from a central drum 352 of the spool 350, wherein the medical tubing is wound around the central drum 352 and between the inner and outer plates 356 and 354. Preferably, the spool 350 is removably mounted on the mounting cylinder 360 and removable from the housing 310, allowing the spool 350 to be replaced with a new spool 350 when needed.

Similarly to the previous embodiment, the medical tubing housing device 300 further includes a receiving collar 340, best shown in FIGS. 11 and 13. The receiving collar 340 is carried by the housing 310 and extends into the internal cavity 361 of the mounting cylinder 360. The housing 310 further includes a fluid inlet 344 for the passing therethrough of a fluid from outside the housing 310 into the housing 310. As shown in FIG. 13, the receiving collar 340 is hollow and include a bore 342 which is in fluid communication with the fluid inlet 344. Also similarly to the previous embodiment, the medical tubing housing device 300 includes a connecting portion rotatably attaching the second end of the medical tubing to the receiving collar 340; however, unlike the previous embodiment (in which the connecting portion takes the shape of a nipple 234), the connecting portion of the present embodiment takes the form of a preferably rigid, U-shaped connector 334 having a first end 336 coupled to the receiving collar 340, wherein at least one circumferential sealing gasket 346 is positioned between the receiving collar 340 and the connecting portion and provides fluid-tightness to the connection between the receiving collar 340 and connecting portion. In turn, a second end 338 of the U-shaped connector 334 is arranged outside the receiving collar 340 and within the drum 352 of the spool 350. When the medical tubing (not shown) is wound on the spool 350, the internal or second end of the medical tubing can extend through an opening 353 in the drum 352 and connect the second end 338 of the U-shaped connector 334.

Similarly to the previous embodiment, the medical tubing housing device 300 further includes a retraction mechanism positioned within the internal space 311 of the housing 310, to cause the spool 350 to rotate in a winding direction (indicated in FIG. 12 by arrow "B"). The retraction mechanism comprises a spiral torsion spring 394. An inner, first end 396 of the spiral torsion spring 394 is connected to the housing 310, and more particularly, to a receiving section or clip 400 which protrudes from the rear housing portion 322. In turn, an outer, second end 398 of the spiral torsion spring 394 is configured to apply a torque on the spool 350 to cause the rotation of the spool 350 in the winding direction (arrow "B") and cause the medical tubing to retract into the housing 310 and wind onto the spool 350. Similarly to the previous embodiment, the retraction mechanism further comprises a drive plate 410 arranged between the rear housing portion 322 and the spool 350. The spiral torsion spring 394 is arranged within a space 412 delimited by a rear face 414 of the drive plate 410 and a circumferential flange 416 extending rearwardly from the rear face 414 of the drive plate 410. The second end 398 of the spiral torsion spring 394 is configured to apply a torque on the drive plate 410, and more specifically on a tab 418 of the drive plate 410 which protrudes into the space 412 and is best shown in FIG. 12. The drive plate 410 is rotatable in unison with the spool 350 by having two protrusions 420 of the drive plate 410 engage with two corresponding holes 358 in the inner plate 356 of the spool 350; in consequence, the drive plate 410 can transfer the torque to the spool 350.

In operation, a user pulls on the second end of the medical tubing outwardly from the housing 310 and causes the spool 350 to rotate in an unwinding direction (arrow "A" in FIG. 12) opposite to the winding direction (arrow "B"), to feed medical tubing from the medical tubing housing device 300 and utilize the medical tubing for medical purposes. In pulling the medical tubing outward, the medical tubing moves the spiral torsion spring 394 from a first unstressed condition to a second stressed condition in which the spiral torsion spring 394 is compressed. In the stressed condition, the second end 398 of the spiral torsion spring 394 pushes on the tab 418 of the drive plate 410 applying a rotation torque on the drive plate 410 in the winding direction (arrow "B"), biasing the spool 350 to rotate jointly with the drive plate 410 in the winding direction (arrow "B").

Similarly to the previous embodiment, the inlet 344 is arranged on a rear side of the rear housing portion 322 as best shown in FIG. 12. Preferably, as shown, the inlet 344 extends outwardly from the housing 310 at a right angle relative to the rear side of the housing 310, to allow the housing 310 to be attached adjacent to a wall or other surface, leaving a minimal gap therebetween.

Figure 15:
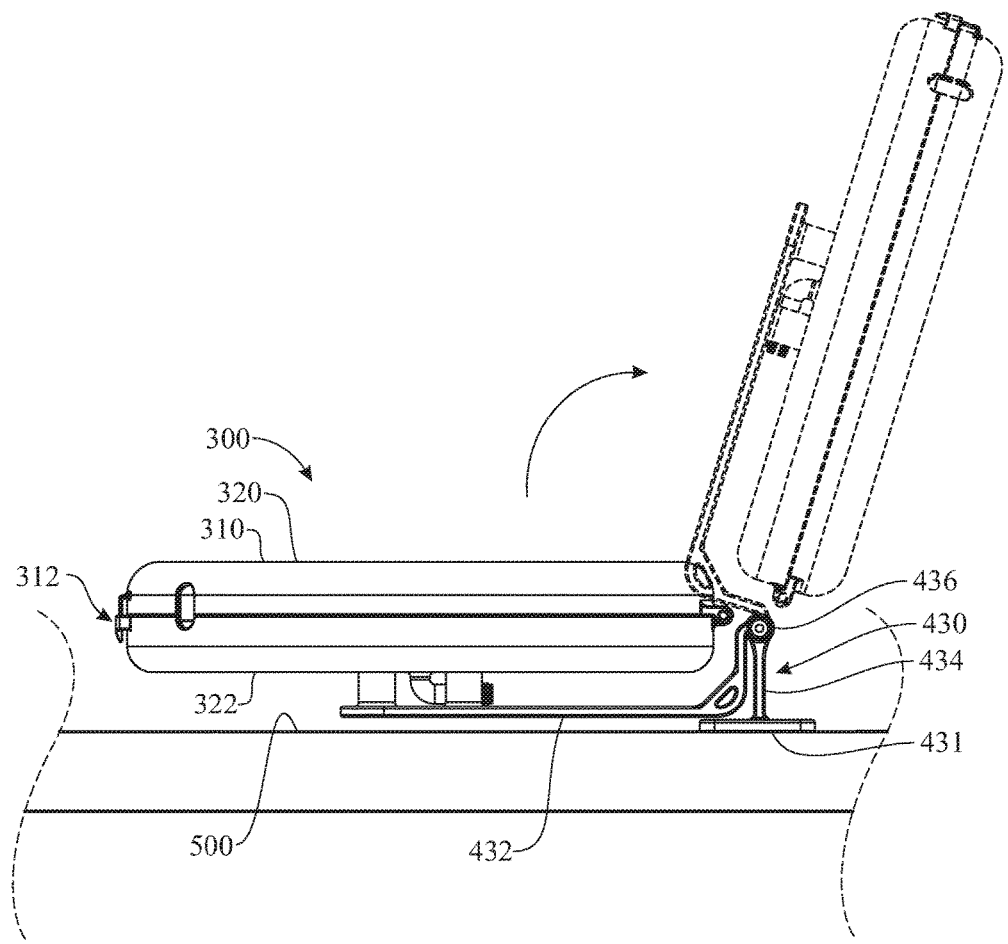
FIG. 15 presents a top plan view of a medical tubing housing device in accordance with a third illustrative embodiment of the invention, including a pivotable wall mount.

The illustration of FIG. 15 shows a variant of the medical tubing housing device 300 of the previous figures. In this variant, the medical tubing housing device 300 further includes a wall mount 430 attached to the rear housing portion 322 of the housing 310. The wall mount 430 is provided with a flat rear side 431 (similarly to the flat rear side 131 of the wall mount 130 of FIG. 6) for resting on a wall 500 or other flat surface. Bolts, screws or other applicable fasteners (not shown) can be inserted through the wall mount 430 to secure the wall mount 430 to the wall or other flat surface, as known in the art. Preferably, as shown, the wall mount 430 can include a first wall mount portion 432 and a second wall mount portion 434 pivotably attached to one another by an articulated connection 436 (e.g. a hinge, ball joint, etc.). The first wall mount portion 432 is attached to the rear housing portion 322, while the second wall mount portion 434 provides the aforementioned flat rear side 431.

Figure 16:
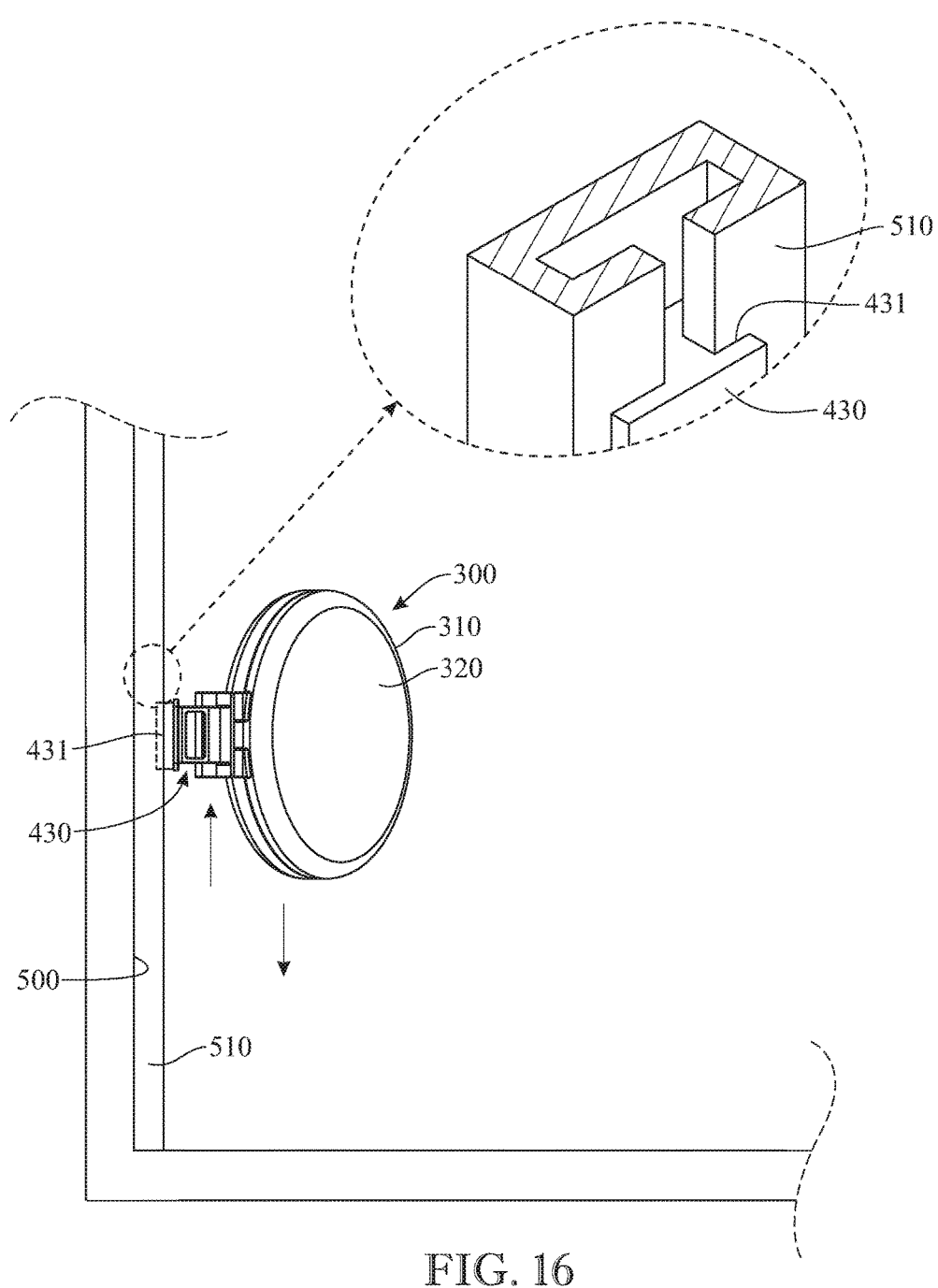
FIG. 16 presents a side elevation view of a variant of the medical tubing housing device of FIG. 15, with the wall mount adjustably assembled to a vertical track.

Further, as shown in FIG. 16, the second wall mount portion 434 can optionally be attached to a vertical C-shaped track 510 which is in turn secured to the wall 500. By adjusting the relative vertical position of the medical tubing housing device 300 and the track 510, the vertical position of the medical tubing housing device 300 along the wall 500 can easily be set in accordance with the user's needs.

Though not specifically shown in FIGS. 11 through 16, the inner plate 356 and the outer plate 354 of the spool 350 can be separated from one another a distance which is less than three times a diameter of the medical tubing, and preferably also greater than twice the diameter of the medical tubing.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A medical tubing housing device for retractably housing a medical tubing for supplying a flow of a fluid to a remote device, comprising:
 a housing delimiting an internal space, the housing comprising a mounting cylinder projecting into the internal space, the mounting cylinder comprising an internal cavity;
 a spool housed within the internal space of the housing and rotatably mounted on the mounting cylinder, the spool carrying a medical tubing, the medical tubing having a first end extending out of the housing and a second end;
 a receiving collar carried by the housing and extending into the internal cavity of the mounting cylinder, wherein the receiving collar is in fluid communication with a fluid inlet of the housing;
 a connecting portion rotatably attaching the second end of the medical tubing to the receiving collar, the connecting portion comprising a rigid, U-shaped connector having a first end coupled to the receiving collar and a second end arranged within the drum of the spool and connected to the second end of the medical tubing; and
 a retraction mechanism positioned within the internal space of the housing, the retraction mechanism including a spiral torsion spring, wherein a first end of the spiral torsion spring is connected to the housing and a second end of the spiral torsion spring is configured to apply a torque on the spool in a winding direction in which the medical tubing is wound into the housing and onto the spool, such that pulling the medical tubing out of the housing rotates the spool in an unwinding direction opposite to the winding direction and moves the spiral torsion spring from a first unstressed condition to a second stressed condition in which the spiral torsion spring biases the spool to rotate in the winding direction.

2. The medical tubing housing device of claim 1, wherein the retraction mechanism further comprises a drive plate, wherein the second end of the spiral torsion spring is configured to apply a torque on the drive plate, and further wherein the drive plate is configured to transfer the torque to the spool and is rotatable in unison with the spool.

3. The medical tubing housing device of claim 2, wherein the spiral torsion spring is arranged within a space delimited by a rear face of the drive plate and a circumferential flange extending rearwardly from the rear face of the drive plate.

4. The medical tubing housing device of claim 1, wherein the inlet extends outwardly from the housing at a right angle relative to the housing.

5. The medical tubing housing device of claim 1, wherein the housing comprises a first housing portion and a second housing portion, the first housing portion arranged frontward of the second housing portion and movable relative to the second housing portion from a closed position in which the first housing portion prevents access to the internal space of the housing to an open position in which the first housing portion is moved away from the second housing portion and allows accessing the internal space of the housing.

6. The medical tubing housing device of claim 5, wherein the mounting cylinder protrudes from the second housing portion.

7. The medical tubing housing device of claim 5, wherein the first housing portion is pivotably connected to the second housing portion.

8. The medical tubing housing device of claim 5, wherein the inlet is arranged on a rear side of the second housing portion.

9. The medical tubing housing device of claim 5, wherein the spiral torsion spring is connected at the first end thereof to the second housing portion.

10. The medical tubing housing device of claim 5, wherein the retraction mechanism is positioned between the spool and the second housing portion.

11. The medical tubing housing device of claim 5, wherein the housing comprises a latch mechanism including a first latch member on the first housing portion and a second latch member on the second housing portion, the first and second latch members engageable to secure the second housing portion in the closed position.

12. The medical tubing housing device of claim 5, further comprising a wall mount attached to the second housing portion, the wall mount comprising a flat rear side for resting on a flat surface.

13. The medical tubing housing device of claim 12, wherein the wall mount comprises a first wall mount portion and a second wall mount portion, wherein the first wall mount portion is attached to the second housing portion, and the second wall mount portion is pivotably attached to the first wall mount portion and comprises the flat rear side.

14. The medical tubing housing device of claim 1, further comprising at least one circumferential sealing gasket positioned between the receiving collar and the connecting portion.

15. The medical tubing housing device of claim 1, wherein the spool is removably mounted on the mounting cylinder and removable from the housing.

16. The medical tubing housing device of claim 1, wherein the spool comprises an inner plate and an outer plate extending in a spaced-apart relationship from a central drum of the spool, wherein the medical tubing is wound around the central drum and between the inner and outer plates.

17. The medical tubing housing device of claim 16, wherein the inner plate and the outer plate of the spool are separated from one another a distance which is less than three times a diameter of the medical tubing.

18. The medical tubing housing device of claim 17, wherein the distance is greater than twice the diameter of the medical tubing.

* * * * *